United States Patent [19]

Ujihara

[11] 4,352,354

[45] Oct. 5, 1982

[54] WINGED RETENTION NEEDLE

[75] Inventor: Yoshio Ujihara, Nara, Japan

[73] Assignee: Nissho Corporation, Osaka, Japan

[21] Appl. No.: 240,596

[22] Filed: Mar. 4, 1981

[30] Foreign Application Priority Data

Oct. 30, 1980 [JP] Japan .................. 55-155681[U]

[51] Int. Cl.³ .................................................. A61M 5/00
[52] U.S. Cl. ................................................... 128/214 R
[58] Field of Search ................. 128/214 R, 214.4, 221

[56] References Cited

U.S. PATENT DOCUMENTS 3,064,648  11/1962  Bujan .............................. 128/214 R
3,640,275  2/1972   Burke .............................. 128/214 R
4,170,993  10/1979  Alvarez ........................... 128/214 R Primary Examiner—Dalton L. Truluck
Attorney, Agent, or Firm—Armstrong, Nikaido, Marmelstein & Kubovcik

[57] ABSTRACT

A winged retention needle comprising a hollow needle having a beveled edge, a rigid cylindrical hub for fixing and supporting the needle, a flexible winged cylinder for rotatably supporting the hub inserted thereinto, and a means for restricting the rotation of the hub inserted through the winged cylinder so that the hub can rotate only 180°. The rear end portion of the hub protruding from the rear end of the winged cylinder is inserted into a flexible tube as used in blood dialysis or continuous fluid administration so as to prevent forward and backward movements with respect to the winged cylinder, and edge surface facing up of the hollow needle inserted in a blood vessel is easily and surely faced down by 180° rotation of the hub.

4 Claims, 7 Drawing Figures

WINGED RETENTION NEEDLE

BACKGROUND OF THE INVENTION

The present invention relates to a winged retention needle which is indwelt in a blood vessel of a patient for a long period of time, for instance, in blood dialysis and continuous fluid administration.

The winged retention needle is inserted into a blood vessel in the state that the edge surface of a beveled edge of a hollow needle is directed up, and after giving a half turn to the needle, it is fixed and retained in the state that the beveled surface is faced down to prevent the vessel from damage by penetration. However, usual winged retention needles have the disadvantage that the operation thereof is troublesome, since a hollow needle is directly fixed to a winged portion with the edge surface faced up and accordingly the edge surface must be faced down by a half rotation of the winged needle after insertion into blood vessels.

It is an object of the present invention is to provide a winged retention needle which is easy to handle.

A further object of the present invention is to provide a winged retention needle which is capable of facing the edge surface up without any fail.

These and other objects of the present invention will become apparent from the description hereinafter.

SUMMARY OF THE INVENTION

In accordance with the present invention, there is provided a winged retention needle comprising
a hollow needle having a beveled edge at its tip,
a hub made of a hard synthetic resin material for fixing and supporting the base of the hollow needle, the head of the hub having a larger diameter than the remaining portion,
a winged supporting cylinder made of a flexible synthetic resin material for rotatably and frictionally supporting the hub inserted thereinto, the rear end portion of the hub protruding through the winged cylinder to provide a fitting portion to be inserted into a flexible tube, and
a means composed of a set of a groove and a pin movable in the groove for restricting the rotation of the hub such that the hub can only be rotated 180° in the circumferential direction and the edge surface faces up or down when the pin is positioned at either end of the groove.

DETAILED DESCRIPTION

Figure 1:
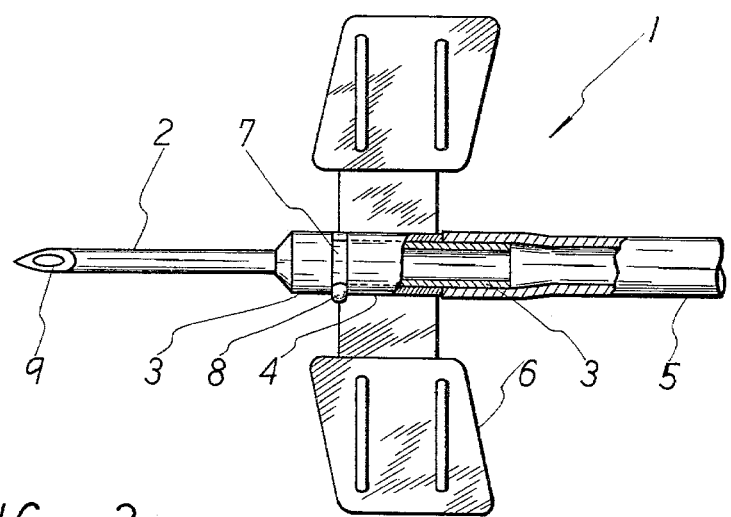
FIG. 1 is a partially cutaway plan view showing an embodiment of the winged retention needle of the present invention.
Figure 2:
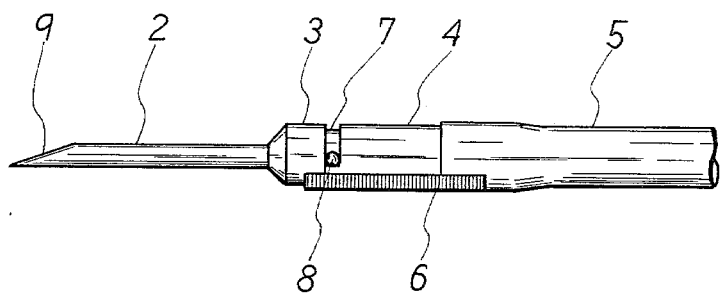
FIG. 2 is a side view of the winged needle of FIG. 1.

Referring now to FIGS. 1 and 2, there is shown an embodiment of the winged retention needle 1 of the present invention. Numeral 2 is a hollow needle having a beveled edge at its foremost end, which is usually made of a stainless steel. The base of the hollow needle 2 is fixed to and supported by a hub 3 with the head having a larger diameter than the cylindrical remaining portion of the hub 3. The hub 3 is usually made of a hard synthetic resin material such as polypropylene or a rigid polyvinyl chloride. Numeral 4 is a flexible winged supporting cylinder for rotatably supporting the hub 3, made of a flexible synthetic resin material such as plasticized polyvinyl chloride or polyethylene. The hub 3 is rotatably, slidably inserted through the winged cylinder 4, and the base end portion of the hub 3 protruding from the rear end of the winged cylinder 4 is inserted to fit into a flexible tube 5 made of a synthetic resin such as plasticized polyvinyl chloride or silicone resin so that the forward and backward movements of the hub 3 are prevented by the tube 5 and the head of the hub with respect to the winged cylinder 4.

In general, flexible wings 6 are integrally formed with the body of the supporting cylinder on both sides thereof, and the shape of the wing is not particularly limited. The wings are preferably provided on the cylinder body to form one plane as shown in FIG. 2. The winged supporting cylinder 4 is provided at the front end with a groove 7 cut away in the circumferential direction extending nearly over a semicircle. On the other hand, the hub 3 is provided with a pin 8 movable in the groove 7 in order to restrict the rotation of the hub 3, and when the pin 8 moves in the groove 7 from one end of the groove to the other end, the hub 3 surely rotates 180°. The pin 8 is usually formed integrally with the hub.

Figure 3:
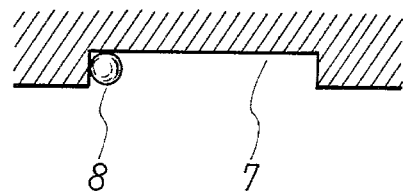
FIGS. 3 and 4 are developed views of a groove as provided in the winged needle of FIG. 1.

The pin 8 is provided on the hub 3 such that when the pin is positioned at either end of the groove 7, an edge surface 9 of the hollow needle 2 is faced up or down. Therefore, the handling of the winged retention needle of the present invention is easy, since after inserting the needle into a blood vessel with the pin 8 positioned at the edge surface facing up end of the groove 7 as shown in FIGS. 1 to 3, the edge surface is faced down by merely rotating the hub 3 until the pin 8 reaches the other end of the groove 7 and the needle is then retained in that state. It is convenient that the pin 8 is provided at a position such that the edge surface is directed down by right-handed rotation from habit.

Figure 4:
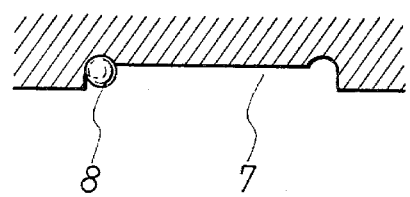

When there is a possibility that the pin 8 freely travels in the groove 7 to turn the needle by a slight force, the width of the groove may be made smaller or the diameter of the pin may be made larger so that the side surface of the pin is brought into contact with the bottom of the groove, and thereby the free rotation of the retained needle is prevented by means of frictional engagement. Also, as shown in FIG. 4, the width of the groove except the both ends may be made smaller than the both ends having a width capable of holding the pin so as to fasten the pin at the both ends, thus securing the handling of the winged retention needle.

Figure 5:
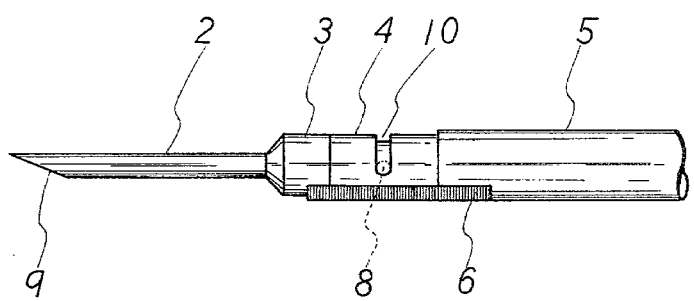
FIG. 5 is a side view showing another embodiment of the winged retention needle of the present invention.
Figure 6:
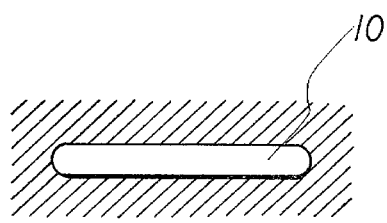
FIGS. 6 and 7 are developed views of a groove as provided in the winged needle of FIG. 5.
Figure 7:
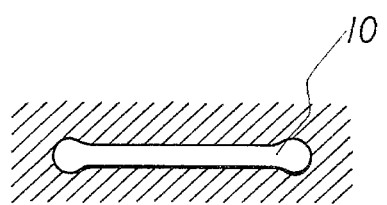

FIG. 5 shows an another embodiment of the winged retention needle of the present invention wherein a slit 10 is provided as a groove in the body of the winged supporting cylinder 4 in the circumferential direction and a pin 8 movable in the slit 10 in a 180° arc is arranged on the hub 3 at a position corresponding to the slit. FIG. 6 is a developed view of the slit portion shown in FIG. 5. As shown in FIG. 7, it is possible to surely fasten the pin 8 to the both ends of the slit 10 by making the slit portion except the both end portions narrower than the both end portions which have a size capable of holding the pin 8, and there is obtained a similar effect to that obtained in the embodiment shown in FIG. 4.

Further, the same effect as in the abovementioned embodiments can be obtained by providing a pin on the inner surface of the winged supporting cylinder and a groove permitting the pin to move in a 180° arc in the hub in the circumferential direction, or by providing a pin at the front end of the winged cylinder and a groove in the rear end portion of the head of the hub.

Although the winged retention needle of the present invention has been described in its preferred embodiments, it is to be understood that the invention is not limited thereto and that various changes and modifications may be made without departing from the spirit and scope of the invention.

What is claimed is:

1. A winged retention needle comprising
   a hollow needle having a beveled edge at its tip,
   a hub made of a hard synthetic resin material for fixing and supporting the base of the hollow needle, the head of the hub having a larger diameter than the remaining portion,
   a winged supporting cylinder made of a flexible synthetic resin material for rotatably and frictionally supporting the hub inserted thereinto, the rear end portion of the hub protruding through the winged cylinder to provide a fitting portion to be inserted into a flexible tube, and
   a means composed of a set of a groove and a pin movable in the groove for restricting the rotation of the hub such that the hub can only be rotated 180° in the circumferential direction and the edge surface faces up or down when the pin is positioned at either end of the groove.

2. The winged retention needle of claim 1, wherein a flexible tube is fitted around the fitting portion protruding from the rear end of the winged supporting cylinder so that the forward and backward movements of the hub are prevented with respect to the winged supporting cylinder by means of the head of the hub and the tube.

3. The winged retention needle of claim 1, wherein the groove and the pin are provided in the body of the winged supporting cylinder and on the hub, respectively.

4. The winged retention needle of claim 1, wherein the groove and the pin are provided in the hub and on the body of the winged supporting cylinder, respectively.

* * * * *